United States Patent [19]

Agrez

[11] Patent Number: 5,266,327
[45] Date of Patent: Nov. 30, 1993

[54] ENHANCED SUTURING AND MEANS THEREFOR

[76] Inventor: Michael V. Agrez, 23 Wrighton Avenue, Bar Beach, Newcastle, New South Wales, 2300, Australia

[21] Appl. No.: 653,348

[22] Filed: Feb. 8, 1991

[51] Int. Cl.⁵ .................. A61L 17/00; A61L 31/00
[52] U.S. Cl. .................. 424/426; 424/423; 424/422; 606/228; 606/230; 530/350; 530/330; 530/300; 514/2
[58] Field of Search .................. 530/300, 330, 350; 514/2; 606/228, 230; 424/422, 423

[56] References Cited

U.S. PATENT DOCUMENTS

| | | | |
|---|---|---|---|
| 4,578,079 | 3/1986 | Ruoslahti | 514/2 |
| 5,013,649 | 5/1991 | Wang | 530/350 |
| 5,061,693 | 10/1991 | Nutt | 530/329 |

OTHER PUBLICATIONS

Cronin et al., *Surg. Gyn. Obstet.*, 126, 747-753 (1968).
Hawley et al., *Br. J. Surg.*, 57, 896-900 (1970).
Wise et al., *Surg. Gyn. Obstet.*, 141, 190-194 (1975).
Pytela et al., *Proc. Natl. Acad. Sci. USA*, 82 5766-5770 (1985).
Burns et al., *Cell*, 45, 269-280 (1986).
Grinnell et al., *J. Cell Sci. Suppl.*, 8 199-209 (1987).
Hynes, *Cell*, 48, 549-554 (1987).
Montesane et al., *Proc. Natl. Acad. Sci. USA*, 85 4894-4897 (1988).
Ravo, *Surg. Clinics N. Amer.*, 68, 1267-1293 (1988).
Nesbitt et al., "In: Leucocyte Typing IV Database and Evaluation Programme," Oxford University Press, 1037 (1989).
Kirchhofer et al., *J. Biol. Chem.*, 265, 615-618 (1990).
Krissansen et al., *J. Biol. Chem.*, 265, 823-830 (1990).
Frelinger III et al., *J. Biol. Chem.*, 265, 6346-6352 (1990).
Smith et al., *J. Biol. Chem.*, 265, 11008-11013 (1990).
Welch et al., *J. Cell Biol.*, 110, 133-145 (1990).
Dedhar et al., *J. Cell Biol.*, 110, 2185-2193 (1990).
Agrez et al., *Br. J. Cancer*, 62, 567-572 (1990).

*Primary Examiner*—Thurman K. Page
*Assistant Examiner*—Sally Gardner
*Attorney, Agent, or Firm*—Scully, Scott, Murphy & Presser

[57] ABSTRACT

The present invention relates to a surgical securing means having releaseably associated therewith a peptide, said peptide comprising the amino acid sequence:

$$[aa]_n\text{-}[RG\text{-}(x)_{n_1}]_{n_2}\text{-}[aa]_{n_3}$$

wherein
R is arginine;
G is glycine;
x is aspartate or glutamate;
aa is any amino acid; and
n is 0–100;
$n_1$ is 0 or 1
$n_2$ is 1–100
$n_3$ is 0–100 and wherein said peptide is released in an amount effective to induce fibroblast-mediated collagen lattice contraction.

16 Claims, 5 Drawing Sheets

ENHANCED SUTURING AND MEANS THEREFOR

FIELD OF THE INVENTION

The present invention relates generally to a method for enhanced suturing in mammals, such as humans. More particularly, the present invention relates to a method for enhanced intestinal anastomosis and to a surgical securing means useful for same.

BACKGROUND OF THE INVENTION

Wound contraction is fundamental to the process of wound healing because it reduces the amount of new tissue required to restore organ integrity after tissue damage. This event is known to be mediated by tissue fibroblasts which are responsible for both the deposition of new matrix and its reorganisation. The biological mediators responsible for these processes include cell-derived growth factors and cell adhesion molecules acting through an array of cell membrane receptors (1). The best characterised of these receptors for extracellular matrix proteins is a family of transmembrane heterodimeric molecules termed integrins (2). These receptors comprise an alpha ($\alpha$) and beta ($\beta$) subunit in noncovalent association and many have been shown to recognize and bind an arginine-glycine-aspartate (referred to as "RGD" using the single letter code) sequence contained within their specific extracellular matrix ligand (3). This supergene family was initially organized into subgroups defined by individual $\beta$ chains, themselves able to associate with multiple $\alpha$ chains, and the particular $\alpha/\beta$ combination determined the ligand specificity. Thus, within the $\beta1$ subgroup there are receptors for laminin, collagen and fibronectin with the specific ligand being determined by the associated $\alpha$ chain (2). More recently, however, it has become clear that the $\alpha$ chain designated as $\alpha v$ can associate with multiple $\beta$ chains, including $\beta1$, $\beta3$ and $\beta5$ (4). Moreover, each of these heterodimeric receptors appears to be able to bind more than one ligand, and at least in the case of $\alpha v \beta 3$ this has been attributed to the relatively high affinity of this complex for the RGD sequence (2,5).

Recently, it has been demonstrated (6) that addition of GRGDSP peptide to the platelet integrin glycoprotein (GP)IIb-IIIa ($\alpha_{IIb}\beta 3$) conferred new binding specificities to this receptor. This event was monitored by the appearance of new antibody-binding domains termed ligand-induced binding sites (LIBS) some of which were shown to be functionally active in being able to induce fibrin clot retraction.

In work leading up to the present invention, the role of LIBS induction was studied in connection with the reorganisation of the extracellular matrix. The in vitro process of collagen lattice contraction has been considered analogous to the process of wound contraction and has been used as a model to test the effects of putative biological mediators (7). In accordance with the present invention, this model was used to assess the ability of the RGD tripeptide recognition signal to induce functional LIBS and the results obtained impact profoundly on an enhanced procedure for wound healing, and in particular, enhanced intestinal anastomosis.

The development of new surgical techniques, suture materials and stapling instruments has not diminished the ever-present challenge for surgeons insofar as intestinal anastomoses continue to be complicated by leakages even in the best hands. This is particularly true for large bowel anastomoses and a recent large multicentre study reported an average clinical anastomotic breakdown rate of 13% with a mortality rate three times higher for such patients compared with patients free of leakage (8,9). The underlying mechanism responsible is the dramatic decrease in the suture-holding capacity of an anastomosis during the first 3-4 days as a result of changes occurring in the extracellular matrix (10,11,12).

Not surprisingly, efforts to understand matrix metabolism at the anastomotic site have centred on collagen, since it is the predominant extracellular matrix protein. Collagen is in a dynamic state of equilibrium in the body and the normal slow turnover is accelerated at sites of wound repair. The breaking strength of an intestinal anastomosis depends on both the amount and quality of existing collagen through which sutures or staples pass. During the first few days after bowel anastomosis, mature collagen is destroyed thereby decreasing the suture-holding capacity of the bowel ends. It is possible, therefore, that intestinal wound healing could be enhanced through the use of biological response modifiers to increase collagen strength by promoting collagen synthesis and/or altering its structure. One means by which the structure of collagen could be altered at the anastomotic site is via fibroblast-matrix attachments. The importance of fibroblasts in the process of wound healing in general is well recognised and forces generated in fibroblasts organise the surrounding connective tissue matrix resulting in wound contraction.

Hence, the ability to influence fibroblast-mediated re-organisation of existing collagen at the anastomotic site in vivo will serve to enhance its suture-holding capacity by condensing the collagen into a more compact and, thereby, stronger meshwork of interlacing fibrils.

In accordance with the present invention, there is provided a surgical securing means which enhances wound healing by means of inducing fibroblasts to condense the collagen matrix around the wound. The present invention is particularly applicable to enhancing intestinal anastomosis.

SUMMARY OF THE INVENTION

One aspect of the present invention relates to a surgical securing means having releaseably associated therewith a peptide, said peptide comprising the amino acid sequence:

wherein
R is arginine;
G is glycine;
x is aspartate or glutamate;
aa is any amino acid; and
n is 0–100;
$n_1$ is 0 or 1
$n_2$ is 1–100
$n_3$ is 0–100
and wherein said peptide is released in an amount to induce fibroblast-mediated collagen lattice contraction.

Another aspect of the present invention contemplates a method for enhanced intestinal anastomosis comprising suturing said anastomosis with a surgical securing means having releasably associated therewith a peptide, said peptide comprising the amino acid sequence:

as defined above.

In a preferred embodiment, the surgical securing means is in a form of sutures and/or surgical staples. In a most preferred embodiment, the sutures, staples and/or other surgical securing means are biodegradable. The present invention is applicable to mammals and in particular humans.

BRIEF DESCRIPTION OF THE FIGURES

Preparation of collagen gels and estimation of gel contraction was identical to that described for FIG. 3a with the exception of higher fibroblast density (14×10$^3$ cells per gel) and higher antibody concentrations: 23C6 (Fab), 45 µg/ml; QE2E5, 18 µg/ml. The inhibitory effects of the antibodies on gel contraction are expressed as residual [$^3$H]$_2$O within gels.

The following single letter abbreviations for amino acid residues are used in the specification and claims:

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

DETAILED DESCRIPTION OF THE INVENTION

The present invention provides a surgical securing means having releaseably associated therewith a peptide in an amount effective to induce fibroblast-mediated collagen lattice contraction. The peptide comprises the amino acid sequence:

$$[aa]_{n}\text{-}[RG\text{-}(x)_{n_1}]_{n_2}\text{-}[aa]_{n_3}$$

wherein

R is arginine;

G is glycine;

x is aspartate or glutamate;

aa is any amino acid; and n is 0–100;

$n_1$ is 0 or 1

$n_2$ is 1–100

$n_3$ is 0–100

Hereinafter, such a peptide will be referred to as an "RGx peptide" which has the same meaning as above. In a preferred embodiment $n_1$ is 0 or 1, n and $n_3$ are separately 0–10 and $n_2$ is 1–5.

In accordance with the present invention, it has been surprisingly discovered that RGx peptides induce colon fibroblast-mediated collagen lattic contraction by exposing functional ligand-induced binding sites (LIBS) on integrin cell membrane receptors. This finding indicates that the RGx peptide-induced LIBS expression implicit in wound healing represents a general biological process of central significance in matrix-mesenchymel interactions with the mammalian, for example human, intestine.

This discovery has profound implications for surgery in general, and in particular intestinal surgery, given the significant morbidity and mortality associated with current anastomotic techniques.

It should be noted that although the present invention is described using intestinal anastomosis, which up to the present time provides the most useful results, this is done with the understanding that the method and surgical securing means described herein is applicable to other forms of surgery and wound healing, all of which we encompassed by the present invention. For example, the RGx peptides could be used with screws and in particular adsorbable screws in relation to achieving opposition and retention of skeletal tissue. In this case the release of the RGx peptide would be around boney cortices and perisosteum enabling more secure screw retention. Furthermore, the present invention is particularly applicable for use in humans but also applies to all other suitable mammals such as livestock and domestic animals.

According to the present invention, therefore, suturing, and in particular intestinal anastomosis, would involve the use of surgical securing means having releasably associated therewith a peptide as hereinbefore defined which is capable of fibroblast-mediated collagen lattice contraction. The condensation of existing collagen surrounding intestinal sutures, for example, by means of RGx peptide induced LIBS expression will enhance the suture holding capacity of the bowel at its united ends.

Preferably, the surgical securing means comprises filaments in the form of sutures or surgical staples although other suitable tying or securing mechanisms may be used (e.g. silk, catgut, synthetic polymers, adsorbable screws, surgical screws). Even more preferably, the surgical securing means including sutures and staples are biodegradable although this is not critical to the practice of the present invention.

In use of the surgical securing means in accordance with the present invention, the RGx peptide is released from the surgical securing means in the immediate vicinity thereof resulting in induction of adjacent fibroblasts to condense the collagen matrix around the sutures by the mechanism as outlined above.

The peptide of the present invention is coated and/or impregnated onto and/or otherwise releaseably associated with the surgical securing means, such as sutures or staples, so that sufficient (but not excessive) peptide will be released within a 72 hour period, preferably a 58 hour period, more preferably a 48 hour period, even more preferably within a 38 hour period and still more preferably a 24 hour period following the uniting of intestinal ends. The sequence length of the peptide is not critical to the practice of the present invention and may range from 2 amino acids in length to approximately or more than 200 amino acids in length. Furthermore, the peptide which is released from the surgical securing means may only represent a portion of the peptide actually associated with the suture and, hence, a releaseably associated peptide as used herein means that the whole peptide associated with the suture or a portion thereof is releaseable in an amount effective to induce fibroblast-mediated collagen lattice contraction.

Furthermore, the surgical securing means of the present invention may be used in combination with other compounds or molecules which act in synergistic, agonistic and/or additive concert with the RGx peptide. Such compounds or other molecules may be similarly associated with the surgical securing means or may be applied separately before, during or after the suturing procedure. Examples of such additional molecules include human colon cancer cell-derived fibroblast elongation factor disclosed in Australian Patent Application No. PK1526/90.

According to this aspect of the present invention, therefore, the surgical securing means will have releaseably associated therewith the peptide as hereinbefore defined and optionally further having associated therewith one or more molecules having synergistic, agonistic or additive effect on the function of the RGx peptide and/or on wound healing.

In accordance with the present invention, only a low concentration of RGx peptide is required as the effective amount since high concentrations of RGx peptide inhibit colon fibroblast-mediated collagen re-organisation in vitro. In this regard, the effective amount is from about 10 μg to about 10 mg/mm of length of securing means. An important aspect of the association of RGx peptide with the surgical securing means is the releaseability of RGx peptide or functional portion therewith. Hence, the effective amount of RGx peptide is from about 10 to about 400 μg/ml of fluid in the local environment around the suture. The volume of "local environment" is from 10 μl to about 100 ml. Hence, the actual amount of RGx peptide per mm of length of surgical securing means is dependent on the amount of said peptide releaseable therefrom.

Additionally, condensation of existing collagen surrounding sutures will not only enhance the suture-holding capacity of the bowel wall but also prevent transgression of intestinal microflora through suture holes. This will assist in reducing the infective complications of bowel surgery such as anastomotic abscess and peritonitis and, thereby, significantly diminish the postoperative morbidity and mortality currently associated with intestinal anastomosis. The surgical securing means of the present invention may also be used in combination with one of more antibiotics or other antimicrobial agents.

The peptides of the present invention may be synthetic, recombinant or naturally occurring provided they have the RGx amino acid sequence. The RGx amino acid sequence may be represented once in each peptide or may be multiply represented in each peptide. The means for preparing synthetic or recombinant peptides are well known in the art. Furthermore, naturally occurring peptides could, for example, be isolated from the blood or other body fluids. The peptides may also have other molecules associated therewith to aid releaseability, stability, solubility and/or association with the surgical securing means. Additionally, the amino acids may be modified (e.g. oxygenated) or derivatised while still retaining their ability to induce wound healing.

In a most preferred embodiment of the present invention, the surgical securing means for intestinal anatomosis is a biodegradeable suture or staple having associated therewith a peptide, said peptide comprising the amino acid sequence:

wherein
R is arginine;
G is glycine;
x is aspartate or glutamate;
aa is any amino acid; and
n is 0–100;
$n_1$ is 0 or 1
$n_2$ is 1–100
$n_3$ is 0–100
and wherein said peptide is released in an amount to induce fibroblast-mediated collagen lattice contraction. Even more preferably, $n_1$ is 0 or 1, n and $n_3$ are separately 0–10 and $n_2$ is 1–5.

The present invention also provides a surgical securing means packaged for sale, said surgical securing means having releaseably associated therewith an RGx peptide as defined above which is capable of inducing fibroblast-mediated collagen lattice contraction. Such a package may also contain synergistic agonistic or additive molecules associated with, or separate to, the surgical securing means.

The present invention is further described by the following non-limiting examples:

EXAMPLE 1

Materials and Methods

Figure 1A:
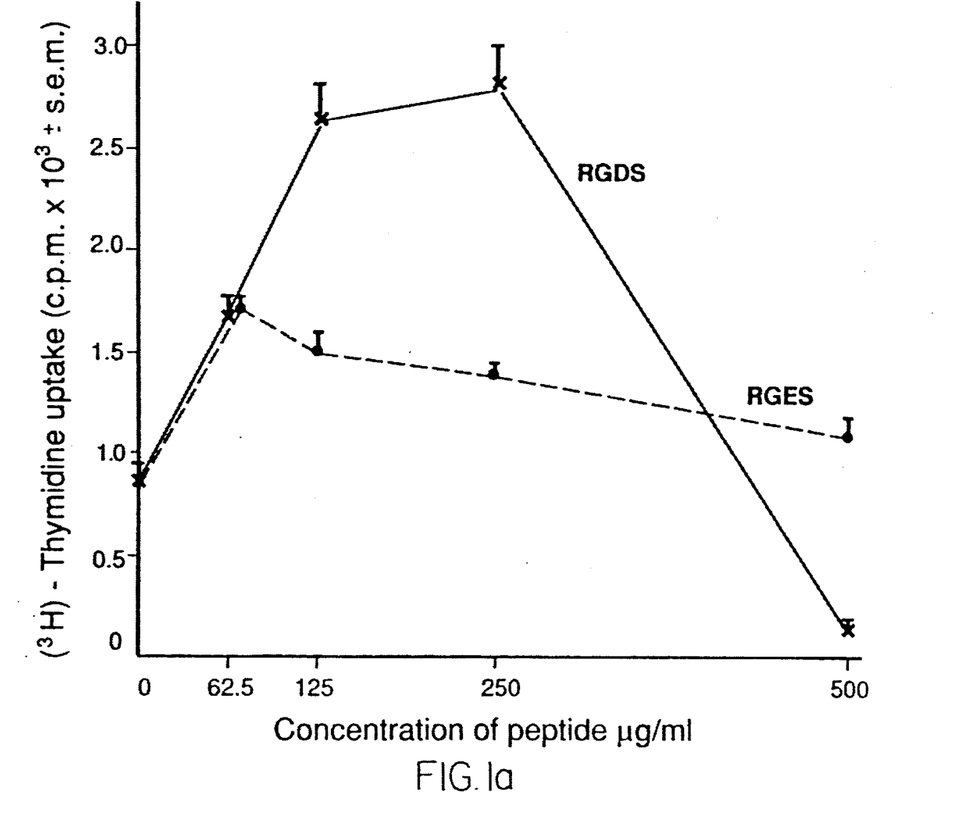
FIGS. 1a and 1b are is a photographic and graphical photographic representations, respectively, showing the effect of increasing concentration of RGDS and RGES peptides on [$^3$H]-thymidine uptake and morphology of colon fibroblasts plated on collagen.
Figure 1B:
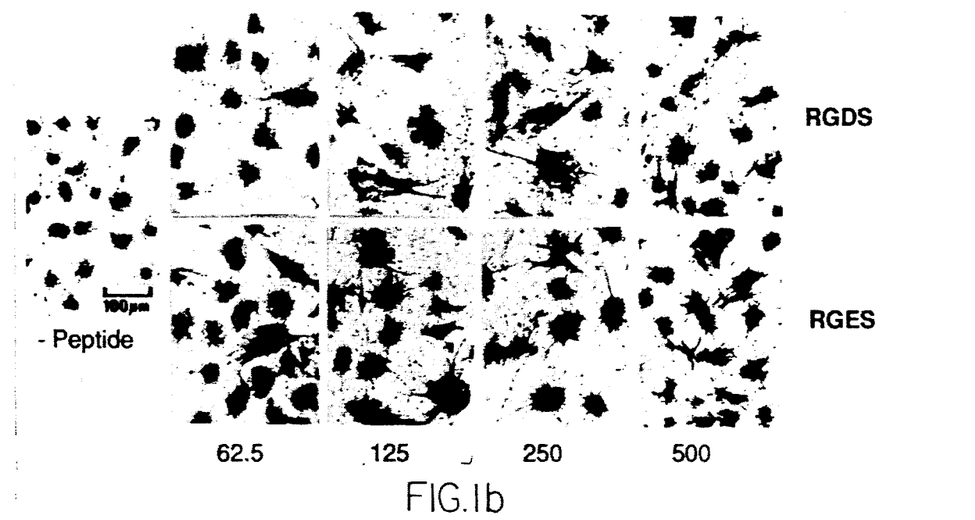

The following methods relate to the Figures:

1. FIG. 1

Collagen gels were prepared in microtitre wells (Linbro, Flow Laboratories) as described below. CCD-18 fibroblasts were seeded on to the collagen in triplicate microtitre wells at a cell density of $2 \times 10^3$ cells/well. Chemically defined serum-free culture medium was used throughout and cultures were incubated at 37° C. in 5% $CO_2$ for 48 hours. Exposure of the cells to peptides (Auspep, Melbourne, Australia) was continuous for the 48 hours and DNA synthesis was estimated by pulsing individual wells with 1 µCi of [$^3$H]-thymidine 24 hours after the initiation of cultures. Cells were harvested at 48 hours by dissolution of the collagen matrix with 25 µl of collagenase (Sigma, Cat. No. C5138; 15 mg/ml in PBS) before automated cell harvesting and measurement of radioactivity. Parallel duplicate microtitre cultures were prepared for visual assessment of fibroblast stretching in the presence of peptides. After 48 hours the cells were fixed and strained with coomassie blue (0.1% w/v solution in 10% v/v acetic acid and 40% v/v methanol). Photomicrography was performed with a 35 mm camera attachment fitted to a Leitz Labovert inverted microscope using technical pan film (Kodak) at 100 ASA setting.

Figure 2A:
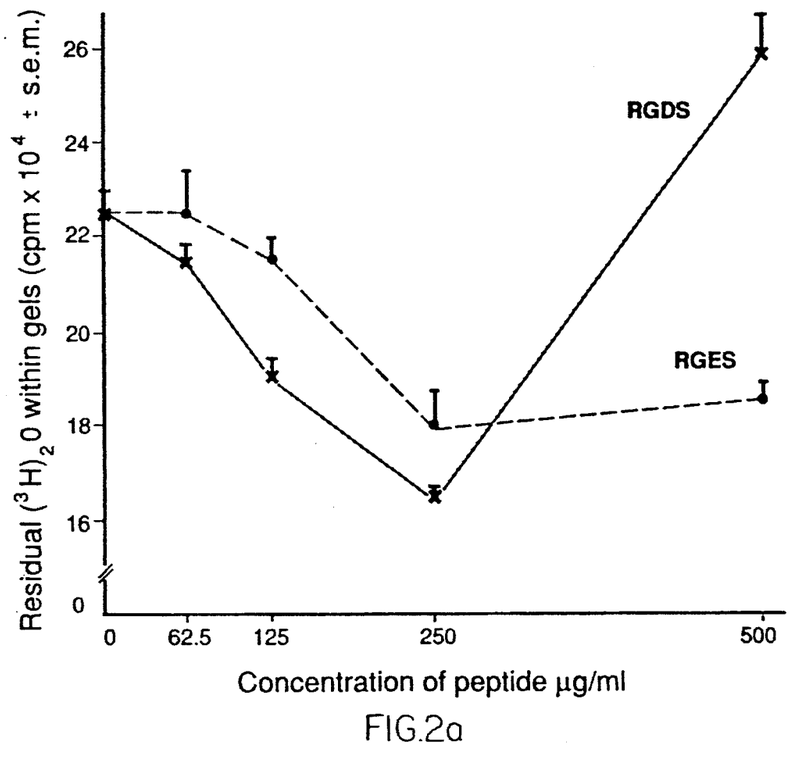
FIGS. 2a and 2b are is a photographic and graphical photographic representations, respectively, depicting the effect of increasing concentration of RGDS and RGES peptides on fibroblast-mediated collagen lattice contraction.
Figure 2B:
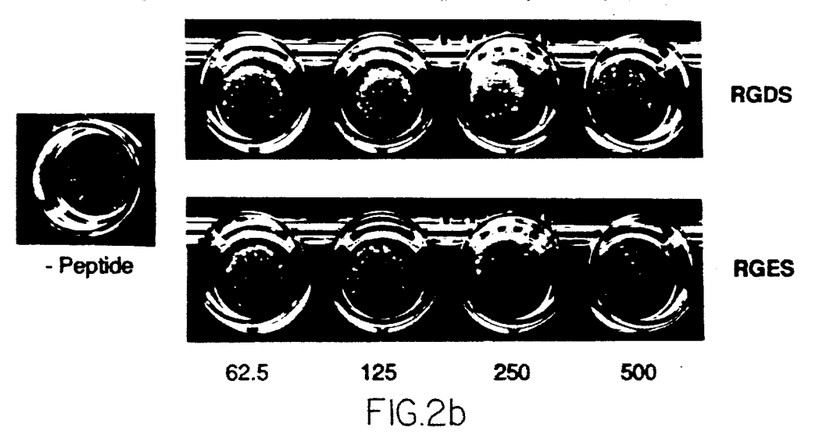

2. FIG. 2

Collagen gels (600 µl) were prepared in 24-well plates (Linbro) in identical manner to that described for the microtitre system except for incorporation of [$^3$H]$_2$O and fibroblasts into the collagen-medium mixture. CCD-18 fibroblasts were seeded into triplicate gels at a cell density of $50 \times 10^3$ cells/gel. Gelled cultures were overlain with 600 µl of serum-free medium containing the peptide and "rimmed" at the plastic interface with a fine needle at the initiation of experiments. The gels were incubated at 37° C. in 5% $CO_2$ and retrieved after 22 hours to quantitate gel volume by measuring the residual [$^3$H]$_2$O within contracted gels (13). Prior to recovery of gels for scintillation counting each gel was photographed using technical pan film (Kodak) at 25 ASA setting.

Figure 3A:
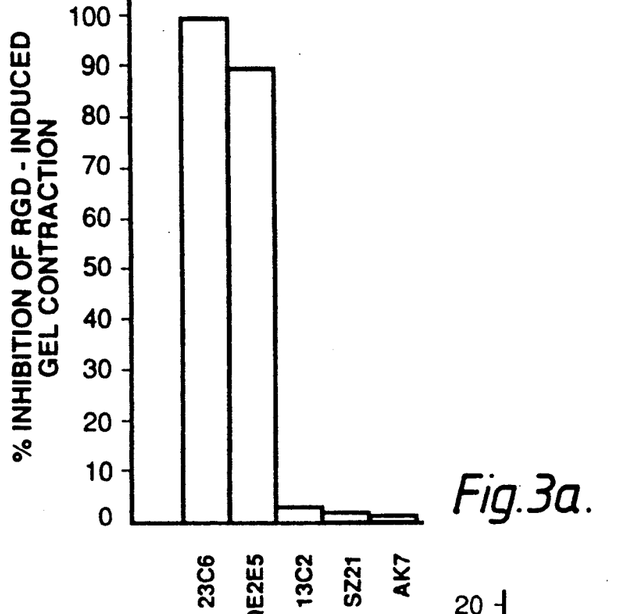
FIG. 3a is a graphical representation showing the effect of selected MAbs on RGDS-induced fibroblast-mediated collagen lattice contraction. The inhibitory effect, if any, is expressed as percentage inhibition of RGD-induced gel contraction relative to uncontracted cell-free control gel volumes. Final concentrations of purified MAbs within wells were: a) 23C6, 30 µg/ml; b) QE2E5, 13 µg/ml; c) 13C2, 29 µg/ml; d) SZ21, 36 µg/ml; e) AK7, 8 µg/ml.
Figure 3B:
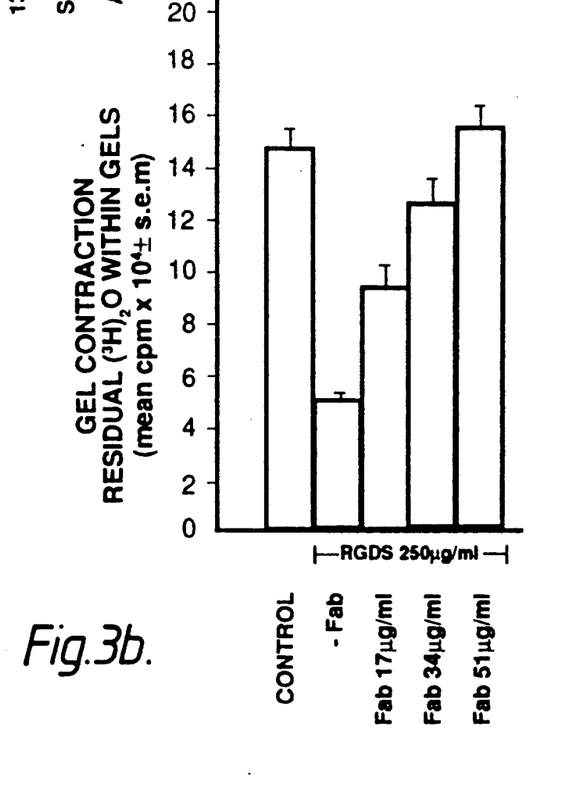
FIG. 3b is a graphical representation showing the dose-response effect of 23C6 Fab fragment of RGDS-induced fibroblast-mediated collagen lattice contraction. Preparation of Fab fragments was as described in Example 1. Preparation of collagen gels and estimation of gel contraction was identical to that described for FIG. 3a. The inhibitors effect of Fab fragment of RGDS (250 µg/ml)-induced contraction is expressed as residual [$^3$H]$_2$O within gels.
Figure 3C:
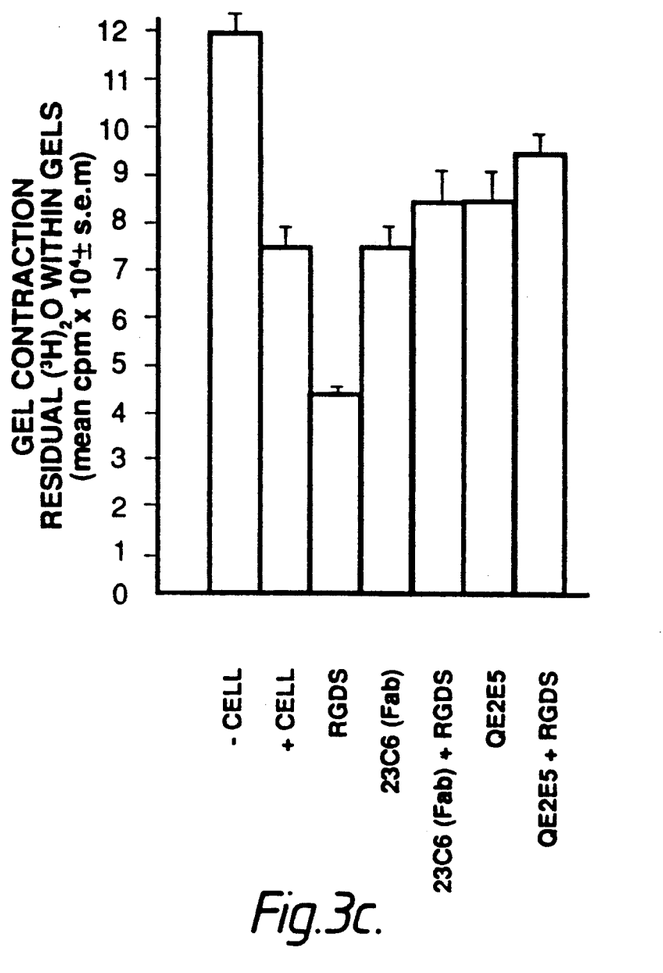
FIG. 3c is a graphical representation showing the effect of the MAbs 23C6 (Fab) and QE2E5 on non-peptide and RGDS-induced (250 µg/ml) collagen gel contraction.

3. FIG. 3

Preparation of collagen gels and estimation of gel contraction was performed in identical manner to that described for the 24-well plates with the exception that 150 µl gel volumes containing $12 \times 10^3$ cells were seeded into quadruplicate microtitre wells for each antibody tested in the presence of RGDS (250 µg/ml final well concentration).

Figure 4A:
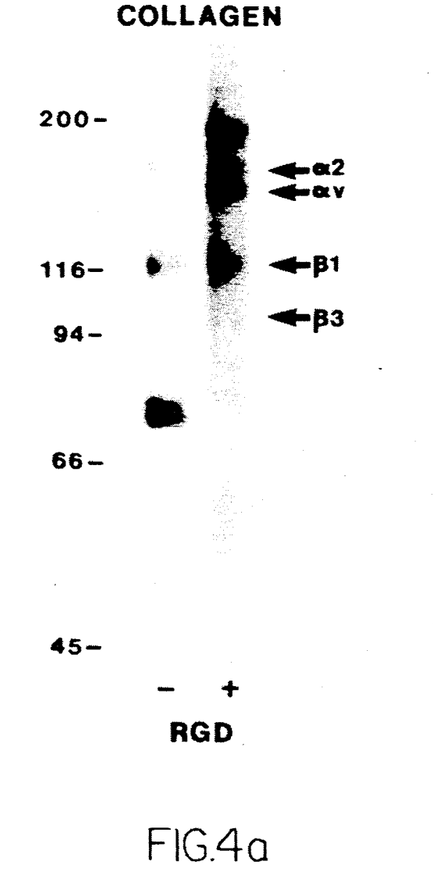
FIGS. 4a and 4b are is a photographic representations depicting collagen binding proteins and 23C6 epitopes, respectively, induced by exposure of cell lysates to RGD-peptide. Left tracks (collagen). Right tracks (23C6) integrins precipitated by the 23C6 antibody from RGD-exposed cell lysates.
Figure 4B:
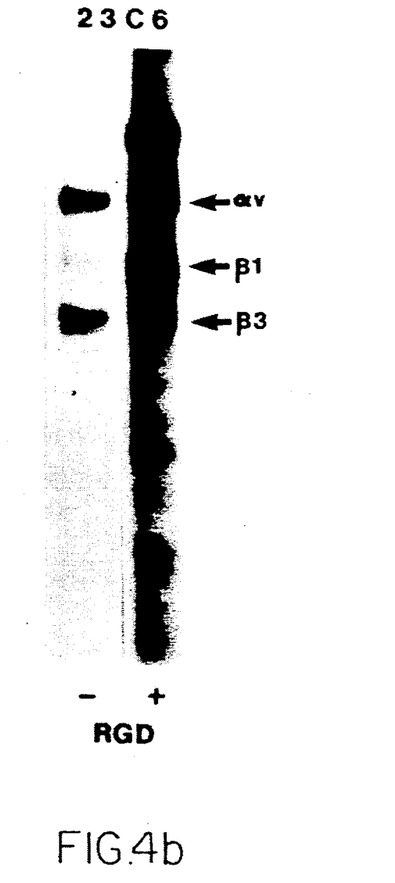

4. FIG. 4

Colon fibroblasts were $^{125}$I labelled on their cell surface, and the lactoperioxidase method used for labelling, as well as the methods used for immunoprecipitation and SDS-PAGE analysis were as we have previously described (14). Cells were lysed in cation-supplemented octylglucoside buffer (10 mM TRIS, 150 mM NaCl, octylglucoside 100 mM containing 1 mM $CaCl_2$), and protease inhibitors (2 mM phenylmethylsulphonyl fluoride; 20 mM iodoacetamide; 50 µg/ml soybean trypsin inhibitor; Sigma Chemicals). The cell lysate was centrifuged (10,000 g for 10 min) and one half (+RGD) incubated with fibronectin-related peptide 1 (-GRGDSP-, Auspep Pty Ltd) at 1 mg/ml concentration for 30 mins. before addition to collagen columns. One milliliter collagen columns were prepared by coupling collagen type I to CNBr-activated Sepahrose 4B beads (Pharmacia). The 1 ml columns were prepared in 1 ml pipette tips plugged with glass wool. Columns were prewashed with 10 volumes of 50 mM. octylglucoside lysis buffer with added $MgCl_2$, $CaCl_2$ and protease inhibitors (as above). The cell lysates with or without RGD peptide (each of 1 ml volume) were applied to the columns and allowed to bind at 4° C. for 18 hours. Columns were then washed with 10 volumes of 50 mM octylglucoside lysis buffer with additives followed by elusion of integrins with 50 mM ethylenediamine tetraacetic acid (EDTA) in 50 mM octylglucoside lysis buffer.

$^{125}$I-labelled cells were lysed in cation-supplemented octylglucoside buffer as above. One half of the lysate (RGD) was incubated together with GRGDSP for 30 min and this and the rest of the lysate (—RGD) were immunoprecipitated with anti-vitronectin receptor (23C6) coupled to Sepharose 4B beads. The antigen-antibody complexes were dissociated by boiling in SDS-PAGE sample buffer (62 mM TRIS, 100 mM SDS, 10% glycerol—pH 6.8). Eluate fractions and immunoprecipitates were analysed reduced and non-reduced by electrophoresis in 7.5% SDS-PAGE followed by autoradiography. The arrowheads indicating the relative molecular weights of $\alpha v$, $\beta 1$ and $\beta 3$ are derived from parallel immunoprecipitation experiments using the same cell lysates. The relative molecular weight markers are myosin heavy chain (200 kD), $\beta$-galactosidase (116 kD), phosphorylase B (94 kD), and albumin (66 kD), and ovalbumin (45 kD).

Other methods referred to herein are as follows:

Native type I collagen was prepare by acetic acid extraction from rat tail tendon; collagen gels were prepared by mixing type I collagen (2.5 mg/ml) with a $\times 2$ concentrate of chemically-defined serum free medium comprising Dulbecco's Modified Eagle's Medium (DMEM, Flow Laboratories, VA, USA) supplemented with glutamine, hydrocortisone, non-essential aminoacids, mercaptoethanol, insulin, transferrin selenium, and antibiotics (penicillin and streptomycin), pH 7.2–7.4. The cell-free collagen gels (100 µl per well) were incubated at 37° C. for 30 minutes to allow time for the collagen to set. Colon fibroblasts were harvested from monolayer flask cultures using 0.05% w/v trypsin, 0.02% w/v ethylenediaminotetracetic acid (Flow Laboratories), washed once in serum-containing medium, then three times in serum-free medium before estimation of cell viability with 0.4% trypan blue solution. Cells were dispensed as 170 µl aliquots into each microtitre well followed by addition of 30 µl of peptide in phosphate buffered saline (PBS).

FAb fragments were prepared as follows: ascites fluid containing the MAb 23C6 (IgG$_1$), was precipitated with 45% w/v ammonium sulphate and resuspended in 100 mM sodium acetate (pH 5.5) to a final concentration of 5 mg/ml. This was dialysed to remove ammonium sulphate and cysteine and ethylenediaminotetracetic acid (EDTA) added (final concentrations: 50 mM cysteine, 1 mM EDTA). The antibody was exposed to 10 µg papain (Sigma, St. Louis, Mo. USA) per milligram of antibody at 37° C. for 12 hours.

Iodoacetamide was then added to a final concentration of 75 mM with further incubation at room temperature for 30 minutes. Fab fragments were separated from Fc fragments and any residual MAb on a protein A-Sepharose column (CL-4B, Pharmacia, Sydney, Australia) using PBS (pH 7.0). The purity of Fab fragments was confirmed by SDS-PAGE and silver staining.

Monoclonal antibodies (13C2) to the αv subunit and 23C6 to the αvβ3 complex were a kind gift from Dr Michael Horton of the Imperial Cancer Research Fund, London; and anti-β3 subunit (SZ21), anti-α2 (AK7), and rabbit anti-β3 antibodies were kind gifts from Dr Michael Berndt of the Department of Medicine, Westmead Hospital, Sydney, Australia. The LM609 and LM142 antibodies to αvβ3 complex and αv subunit were kindly supplied by Dr David Cheresh, Scripps Clinic and Research Foundation, CA; the IA7 and IE8 antibodies to platelet glycoprotein IV by Dr Andrew Boyd, Walter and Eliza Hall Institute of Medical Research, Melbourne; and the antibody to the β1 subunit (QE2E5) was a kind gift from Dr Graeme Russ of the Queen Elizabeth Hospital, Adelaide, Australia.

EXAMPLE 2

Human diploid colon fibroblasts (CCD-18, American Type Culture Collection, Rockville, MD, USA) were seeded on collagen type I gels under serum-free conditions, in the presence or absence or RGx peptides, such as RGD-containing peptides. At relatively low concentrations of the peptide, a dramatic dose-related increase in cell stretching was observed (FIG. 1). The phenomenon of cell stretching has been shown to parallel DNA synthesis. Hence, to quantitate the effect of the peptide, fibroblast cultures were exposed to increasing concentrations of RGDS and DNA synthesis measured by the incorporation of tritiated thymidine. The dose-related stretching seen in the presence of RGD peptide was also obtained in this quantitative assay (FIG. 1). High concentration of peptide (500 μg/ml) resulted in inhibition of cell stretching and reduced thymidine uptake to levels below that of cells in the absence of peptide (FIG. 1). The phenomenon of cell stretching has also been shown to be linked to the ability of fibroblasts to induce collagen lattice contraction (13). Therefore, the effect of RGD-containing peptides on fibroblast-induced collagen lattice contraction was also measured. Both visually and quantitatively (using tritiated water) there was a dose-related induction of collagen gel contraction by RGD peptide to a concentration of peptide (250 μg/ml). High concentration of peptide (500 μg/ml) inhibited contraction to less than that seen in the absence of peptide (FIG. 2). In both the cell stretching and gel contraction assays the RGES peptide caused similar but significantly less biological effect, and high dose inhibition did not occur (FIGS. 1 and 2).

To determine which receptors were involved in RGD-induced cell stretching and gel contraction the inventor attempted to inhibit this effect with a panel of monoclonal antibodies. Inhibition of spreading was assessed visually in the presence of antibodies to αv (LM 142, 13C2), β3 (SZ21 and rabbit polyclonal antibody), β1 (QE2E5), α2 (AK7) and the αvβ3 complex (LM609, 23C6), as well as antibodies to a platelet collagen receptor, GPIV (IA7, IE8). Only antibodies to αv, β1 and the αvβ3 complex were inhibitory. Their effectiveness in inhibiting RGD-mediated effects was confirmed in the gel contraction assay with selected antibodies (FIG. 3a) and the Fab fragment of one of the antibodies so tested (23C6) was found to be equally effective in a dose-dependent manner (FIG. 3b). It is of interest that the effect of the antibody against β1 (QE2E5), like that of high dose RGD peptide seen above, was to inhibit contraction to less than that seen with gels in the absence of peptide (FIG. 3c). The integrin α2β1 has been clearly demonstrated to function as a collagen receptor in a number of cell types (15). Collagen binding mediated by this receptor is RGD dependent but relatively high concentrations of free peptide are required to displace this integrin from collagen affinity columns, and this is probably a reflection of the fact that the β1-associated integrins exhibit a 10 to 100-fold lower affinity for the peptide ligand than does the β3-associated vitronectin receptor. It is, therefore, considered likely that the small amount of cell spreading seen on collagen and the collagen lattice contraction observed in the absence of low dose RGD peptide might be attributable to constitutively expressed α2β1 integrin and that such α2β1-mediated spreading was inhibited only by high concentration of RGDS peptide. This was supported by the observation that RGDT inhibited spontaneous (non-peptide-induced) gel contraction to a greater degree than RGDS peptide consistent with the known higher affinity of this particular integrin for RGDT than RGDS. Moreover, at high concentration the antibody QE2E5 directed against the β1 subunit was more effective in inhibiting spontaneous contraction than the antibody 23C6 to the αvβ3 complex (which very effectively inhibited peptide-induced contraction (FIG. 3c).

To determine directly the polypeptides involved in collagen binding, affinity chromatography was carried with collagen type I columns. The fibroblasts were labelled on the cell surface with $^{125}I$, solubilized in octylglucoside and allowed to bind to the collagen in the presence or absence of RGDS peptide. In the absence of peptide the collagen binding proteins presented a profile which was essentially identical to that previously described (15) and by immunoprecipitation with monoclonal antibodies the inventor was able to identify the two major integrin bands as α2 and β1. In the presence of RGDS, several additional bands were seen to bind to the collagen column (FIG. 4). One of these bands was clearly identified as αv by immunoprecipitation; and there was an obvious increase in the amount of β1 subunit without a corresponding increase in α2. There was also a diffuse band observed at around 90 kD (FIG. 4) which showed an increase in apparent molecular weight upon reduction: this band showed the same migration pattern as β3, since it appears to be a β chain associated with αv, the possibility that it might be β5 cannot be excluded. In three experiments, the amount of β3/β5 band recovered from the collagen affinity columns varied considerably but it was always much less prominent than the bands corresponding to αv and β1.

An apparent anomaly between the data from collagen chromatography and those from the inhibition studies is that the inhibitory antibodies LM609 and 23C6 specifically identify the αvβ3 complex (16) yet this complex is not prominent among the collagen binding proteins. This apparent contradiction is perhaps resolved by the data shown in FIG. 4. In the absence of RGD peptide, 23C6 specifically immunoprecipitates αvβ3, but in the presence of peptide the antibody precipitates αv together with multiple β chains. In parallel immunoprecipitation experiments one of these associated β chains could be identified as β1, and another as β3, but a suitable precipitating antibody to β5 was not available for this study and the presence of this subunit cannot be excluded. The additional band at around 200 kilodaltons was not identified although its apparent molecular weight would be consistent with identity to β4. Horton and colleagues (17) have shown that the epitope bound by 23C6 is on the αv subunit but its expression is dependent upon complex formation with β3. It is postulated here that expression of this cryptic epitope on αv can be induced by association with other β subunits in the presence of RDG peptide. In this regard, the 23C6 epitope is considered as a LIBS and the inhibition studies here clearly show that this LIBS is intimately involved in collagen gel contraction by fibroblasts.

In accordance with the present invention, synthetic RGx peptides can enhance fibroblast function in an in vitro model of wound healing. A similar recognition system may exist in vivo in the process of wound contraction. This may explain some of the previously documented wound promoting effects of fibronectin (18). Accordingly, RGx peptide-induced LIBS expression implicit in wound healing may represent a general biological process of central significance in matrix-mesenchymal interactions.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. WELCH M. P., ODLAND G. F. AND CLARK R. A. F., *J. Cell Biol.* 110: 133, 1990.
2. HYNES R. O., *Cell* 48: 549, 1987.
3. DEDHAR S and GRAY V, *J. Cell Biol.* 110: 2185, 1990.
4. KRISSANSEN et al., *J. Biol, Chem.* 265: 823, 1990.
5. PIERSCHBACHER M. D. and RUOSLAHTI E, *Proc. Natl. Acad. Sci. USA* 82: 5766, 1985.
6. FRELINGER III A. L. et al., *J. Biol. Chem.* 265: 6346, 1990.
7. MONTESANO R and ORCI L, *Proc. Natl. Acad. Sci. USA* 85: 4984, 1988.
8. FIELDING L. P., STEWART-BROWN S, BLESOVSKEY L and KEARNEY G, *Br. Med. J.* 2: 422-414, 1980.
9. RAVO B, *Surg. Clinics N. Amer.* 68: 1267-1293, 1988.
10. CRONIN K, JACKSON D. S. and DUNPHY J. E., *Surg. Chynecol. Obstet.* 126: 747-753, 1968.
11. HAWLEY P. R., FAULK W. P., HUNT T. K. and DUNPHY J. E., *Br. J. Surg.* 57: 896-900, 1970.
12. WISE L, McALISTER W, STEIN T and SCHUCK P, *Surg. Gynecol. Obstet.* 141: 190-194, 1975.
13. AGREZ M. V. and CHUA F. K., *Br. J. Cancer* 62: 567, 1990.
14. BURNS G. F. et al., *Cell* 45: 269, 1986.
15. KIRCHHOFER D, LANGUINO L. R., RUOSLAHTI E and PIERSCHBACHER M. D., *J. Biol. Chem.* 265: 615, 1990.
16. SMITH J. W. et al., *J. Biol. Chem.* 265: 11008, 1990.
17. NESBITT S, HART I and HORTON M. A., In: Leucocyte Typing IV Database and Evaluation Programme, Oxford University Press p1037, 1989.
18. GRINNELL F, TODA K and TAKASHIMA A, *J. Cell Sci. Suppl.* 8: 199, 1987.

What is claimed is:

1. A surgical securing means comprising a peptide selected from the group consisting of Arg-Gly-Glu-Ser and Arg-Gly-Asp releasably coated and/or impregnated onto a surgical securing device wherein said peptide is released from said device in an amount effective to induce fibroblast-mediated collagen lattice contraction.

2. A surgical securing means in accordance with claim 1 wherein said surgical securing device is a suture.

3. A surgical securing means in accordance with claim 1 wherein said surgical securing device is a surgical staple.

4. A surgical securing means in accordance with claim 1 wherein said surgical securing device is an adsorbable screw.

5. A surgical securing means in accordance with claim 1, 2 or 3 wherein said surgical securing device is biodegradable.

6. A surgical securing means in accordance with claim 1 wherein said effective amount of said peptide released from said device is from about 10 to about 400 micrograms per ml. of fluid in the local environment around the securing device.

7. A surgical securing means in accordance with claim 1 wherein said peptide is Arg-Gly-Glu-Ser.

8. A surgical securing means in accordance with claim 1 wherein said peptide is Arg-Gly-Asp.

9. A method of intestinal anastomosis comprising intestinal anastomosing with a surgical securing device releasably coated and/or impregnated with a peptide selected from the group consisting of Arg-Gly-Glu-Ser and Arg-Gly-Asp and wherein said peptide is released in an amount effective to induce faberblast-mediated collagen lattice contraction.

10. A method in accordance with claim 9 wherein said surgical securing device is a suture.

11. A method in accordance with claim 9 wherein said surgical securing device is a surgical staple.

12. A method in accordance with claim 9 wherein said surgical securing device is an adsorbable screw.

13. A method in claim 9, 10 or 11 wherein said surgical securing device is biodegradable.

14. A method in accordance with claim 9 wherein said effective amount of said peptide released from said device is from about 10 to about 400 micrograms per ml. of fluid in the local environment around the securing device.

15. A method in accordance with claim 9 wherein said peptide is Arg-Gly-Glu-Ser.

16. A method in accordance with claim 9 wherein said peptide is Arg-Gly-Asp.

* * * * *